(12) United States Patent
Tepic

(10) Patent No.: US 10,076,360 B2
(45) Date of Patent: Sep. 18, 2018

(54) EXTERNAL FIXATOR

(71) Applicant: AKESO AG, Zürich (CH)

(72) Inventor: Slobodan Tepic, Zurich (CH)

(73) Assignee: AKESO AG, Zürich (CH)

( * ) Notice: Subject to any disclaimer, the term of this patent is extended or adjusted under 35 U.S.C. 154(b) by 0 days.

(21) Appl. No.: 15/107,598

(22) PCT Filed: Dec. 24, 2013

(86) PCT No.: PCT/EP2013/077970
§ 371 (c)(1),
(2) Date: Jun. 23, 2016

(87) PCT Pub. No.: WO2015/096861
PCT Pub. Date: Jul. 2, 2015

(65) Prior Publication Data
US 2016/0310167 A1  Oct. 27, 2016

(51) Int. Cl.
*A61B 17/00* (2006.01)
*A61B 5/04* (2006.01)
*A61B 17/64* (2006.01)
*A61B 17/60* (2006.01)

(52) U.S. Cl.
CPC .......... *A61B 17/6458* (2013.01); *A61B 17/60* (2013.01); *A61B 17/645* (2013.01); *A61B 17/64* (2013.01)

(58) Field of Classification Search
CPC ... A61B 17/64; A61B 17/645; A61B 17/6458; A61B 17/6466; A61B 17/6475; A61B 17/6483
See application file for complete search history.

(56) References Cited

U.S. PATENT DOCUMENTS

| | | | | |
|---|---|---|---|---|
| 2,435,850 A | * | 2/1948 | Siebrandt | A61B 17/60 606/54 |
| 5,078,719 A | * | 1/1992 | Schreiber | A61B 17/152 606/87 |
| 5,728,096 A | * | 3/1998 | Faccioli | A61B 17/60 606/54 |
| 5,741,251 A | * | 4/1998 | Benoist | A61B 17/60 606/54 |
| 5,746,741 A | * | 5/1998 | Kraus | A61B 17/171 606/267 |
| 5,803,924 A | | 9/1998 | Oni et al. | |

(Continued)

FOREIGN PATENT DOCUMENTS

| | | |
|---|---|---|
| BE | 389 476 A | 7/1932 |
| CN | 1125557 A | 7/1996 |

(Continued)

OTHER PUBLICATIONS

Search Report cited in PCT/EP2013/077970 dated Mar. 5, 2014, 3 pages.

(Continued)

*Primary Examiner* — Eduardo C Robert
*Assistant Examiner* — Michelle C Eckman
(74) *Attorney, Agent, or Firm* — Rothwell, Figg, Ernst & Manbeck P.C.

(57) ABSTRACT

The invention relates to an external fixator device and the method of its use in treating bone fractures and in orthopedic interventions, such as corrective osteotomies.

11 Claims, 11 Drawing Sheets

(56) References Cited

U.S. PATENT DOCUMENTS

Figure 1:
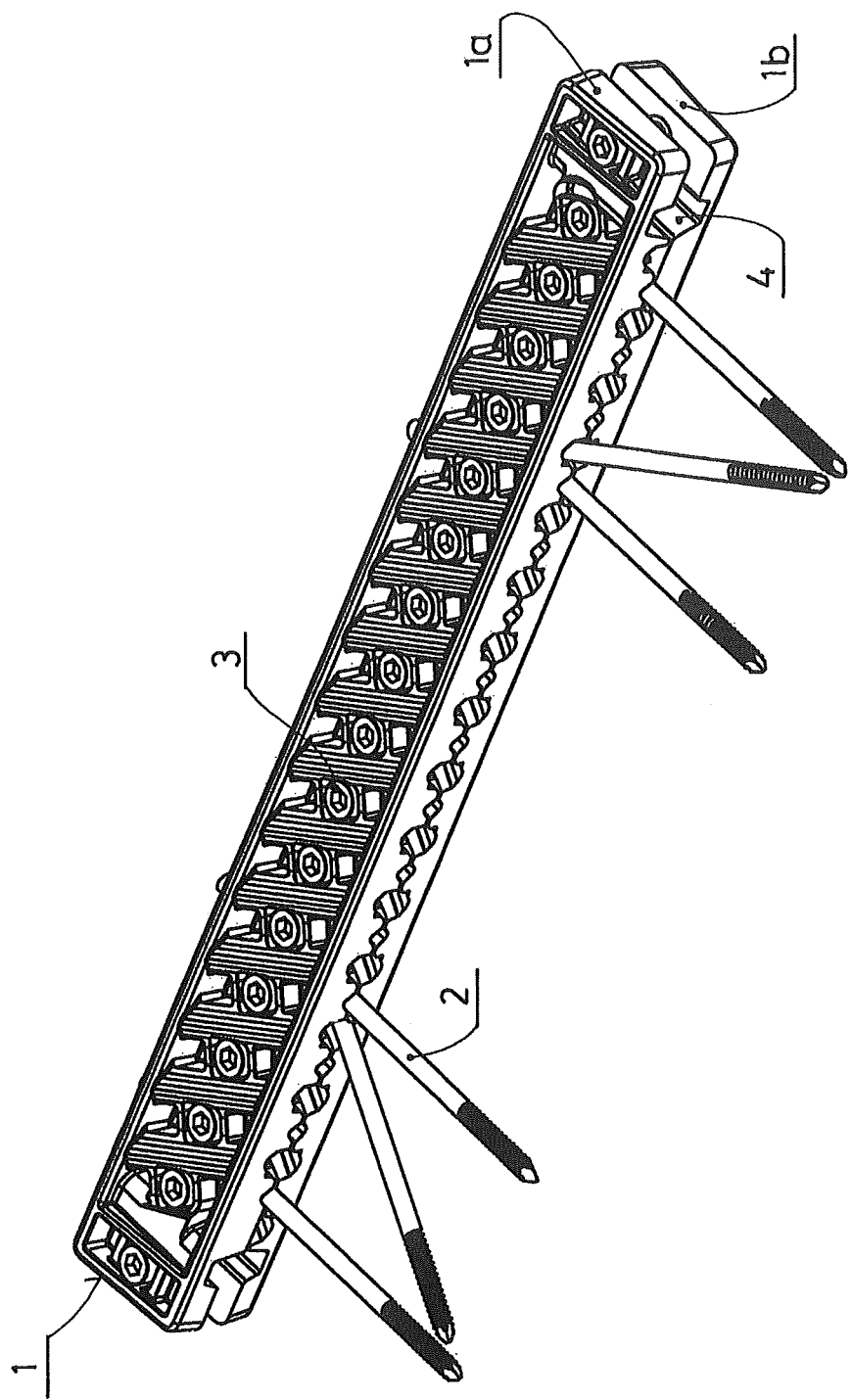

| | | | | |
|---|---|---|---|---|
| 6,565,564 B2* | 5/2003 | Hoffman | ............ | A61B 17/6466 606/59 |
| 7,261,713 B2* | 8/2007 | Langmaid | .......... | A61B 17/6416 606/59 |
| 7,618,417 B2* | 11/2009 | Thomke | ............ | A61B 17/6466 403/329 |
| 7,828,801 B2* | 11/2010 | Mirza | ................ | A61B 17/6416 606/54 |
| 8,262,656 B2* | 9/2012 | Mirza | ................ | A61B 17/6416 606/54 |
| 8,372,125 B2* | 2/2013 | Hansson | ................ | A61B 17/60 606/301 |
| 2011/0172664 A1* | 7/2011 | Bagnasco | .......... | A61B 17/6483 606/59 |
| 2012/0271308 A1* | 10/2012 | Dominik | ............ | A61B 17/7077 606/59 |
| 2014/0257288 A1* | 9/2014 | Chang | ................ | A61B 17/6466 606/59 |
| 2014/0303621 A1* | 10/2014 | Gerold | ............... | A61B 17/6458 606/59 |
| 2016/0310167 A1* | 10/2016 | Tepic | ..................... | A61B 17/60 |

FOREIGN PATENT DOCUMENTS

| | | |
|---|---|---|
| CN | 1571651 A | 1/2005 |
| WO | 95/04504 A1 | 2/1995 |
| WO | 96/05777 A1 | 2/1996 |
| WO | 97/03620 A1 | 2/1997 |
| WO | 03/030759 A2 | 4/2003 |

OTHER PUBLICATIONS

Notification of the First Office Action cited in Application No. 201380080909.6 dated Oct. 30, 2017 (with translation), 12 pages.

* cited by examiner

EXTERNAL FIXATOR

CROSS REFERENCE TO RELATED APPLICATION

This application is a 35 U.S.C. 371 National Phase Entry Application from PCT/EP2013/077970, filed Dec. 24, 2013, the disclosure of which is incorporated by reference in its entirety.

FIELD OF THE INVENTION

The invention relates to an external fixator device and the method of its use in treating bone fractures and in orthopedic interventions, such as corrective osteotomies.

BACKGROUND

Fractured bones and corrective osteotomies are surgically treated by means of one of the three generic medical device families: (1) plates and screws; (2) intramedullary nails, and (3) external fixators. Selection of external fixation by trauma and orthopedic surgeons is greatly influenced by their formation, attitude, place of practice and general economic conditions in addition to the nature of the medical problem to be treated. This greatly complicates any estimates of what the number of cases being treated by any of the methods might be worldwide, but all three are universally considered as fundamentally important surgical aids. Internal fixation by plates or nails is simply not possible in most of the undeveloped world, thus making external fixation the only potentially viable, modern alternative to complement conservative treatments by fracture splinting or casting. Unfortunately, the cost of external fixators produced in the developed world is also prohibitive for most of the undeveloped countries.

The main drawback of external fixation is also rather uncertain and uneven progress of bone healing when compared to internal fixation. Passage of bone pins or wires through soft tissue surrounding the bone and the skin increases the risk of infection when the fixator is kept on the patient for months. Much of the uncertainty can be explained in view of rather recent research findings, which have detailed different biological phases of fracture healing that call for different mechanical conditions at the fracture site. In the very early stages, in the first week or two, as the repair is initiated, differentiating factors emanating from the surrounding bone need to provide signals to the proliferating cells in the fracture zone to actually turn themselves into bone forming cells. In absence of any movement across the fracture, or the osteotomy, mass transport of the signals out of the bone and throughout the zone of repair is limited to diffusion, which may not suffice when the gaps are in excess of some hundreds of micrometers. Formation of fibrous tissue in the gap, which is what tends to quickly fill any tissue defects, may slow down, if not totally frustrate formation of bone proper, leading to delayed unions or non unions. Movement and particularly compression of the gap promotes convective mass transport of the biological factors out of the bone and within the gap, driving the differentiation process towards bone formation.

After this early period, however, once the early organic matrix for bone has been produced and the mineralization starts to set in, excessive movement will prevent bridging of the gaps between the nuclei of mineralization and disrupt the healing process. So now, in order to facilitate a safe and thorough process of mineralization, the movement across the gap should be reduced as much as possible calling for as stiff a construct of the external fixator as possible.

In the final stages of fracture union, presence of the stiff external fixator may hinder remodeling of healed bone by reducing the full physiological loading it will need to support once the fixator is removed, so again, a change in fixator stiffness, back to low, is called for.

There are innumerous ways in which this modulation can be carried out with conventional external fixators, but they all suffer from deficiencies. The fixator of this invention is particularly suited to overcome these deficiencies.

SUMMARY OF THE INVENTION

According to the present invention, an external fixator is provided, which is designed to allow insertion of bone pins in parallel fashion, but also at an angle to each other. The stiffness of the construct with no more than two bone pins parallel to each other is much higher than of that with all pins parallel. This is a simple mechanical fact, frequently ignored by the designers and users of external fixators. Modulation of the overall stiffness can thus be effected by locking either only two, or more than two, e.g. three pins inserted in a bone segment. For the maximum effect of modulation the external frame that holds the bone pins together needs to be as stiff as possible. It also needs to lock the pins very stably against the bending and axial forces.

The fixator of this invention fulfills the mechanical requirements outlined above, but it also solves the problem of production at a cost affordable to even countries of the undeveloped world. Its deployment in the developed world can reduce the overall costs of the medical treatment not only because of the lower price of the hardware, but because and more importantly, if used according to the proposed method, it can shorten the time to healing and avoid unnecessary further surgeries.

A subject-matter of the present invention is an external fixator for fixing bone segments into a construct comprising a frame (1) and a plurality of bone pins (2), wherein the frame (1) consists of two bars (1*a*, 1*b*) opposed to each other in a clamshell fashion and clamped together by a multitude of fastening means, e.g. bolts and nuts (3), and wherein the clamping of the two bars results in clamping of some, but not all of the bone pins interposed between the bars at a multitude of pre-set positions.

The external fixator according to the present invention comprises an external frame composed of two, preferably identical bars and a set of bone pins, which can be inserted through and clamped in the frame at any of a plurality of pre-set positions by fastening elements, e.g. by tightening a set of bolts and nuts spanning the bars of the frame. The bone pins can be placed either perpendicularly to the frame or at an oblique angle to the frame. Clamping together the bars of the frame in a clamshell fashion, fixes the bone pins that are perpendicular to the frame, but not the obliquely positioned bone pins. The obliquely positioned bone pins are locked only upon insertion of fixing elements e.g. shims between the bone pins and the bars of the frame. The perpendicular bone pins may e.g. be located in the mid-plane of the fixator, whereas the oblique bone pins may be located in a plane transverse to the fixator. This allows for modulation of the construct stiffness at desired time points after the fracture has been stabilized by insertion of all of the bone pins into the bone segments.

In a typical configuration, with two parallel bone pins perpendicular to the frame and one oblique bone pin per bone segment, locking the oblique bone pin in addition to the perpendicular bone pins will increase the overall stiffness of the construct 2 to 3 times, depending on the frame intrinsic stiffness. This factor of modulation also depends on the stiffness of the bone pins and the bone itself, but it is invariably much higher than what can be achieved by, for example, additionally locking the third pin in a more conventional configuration with all three pins being parallel to each other, which brings only a fractional increase in construct stiffness.

Properly modulating the construct stiffness between biologically distinct phases of bone healing can dramatically reduce the time of healing and improve the strength of the healed defect. Particularly, and in contrast to the well-accepted notion of dynamization promoted by the company Orthofix in the context of external fixation, an initial period of about one to two weeks with low stiffness of the construct, followed by a period with an increased stiffness of the construct, leads to an outcome superior to what can be obtained by keeping either low or high stiffness throughout the healing process, or to switching from initially high to low stiffness (J Bone Joint Surg Am. 2012 Nov. 21; 94(22): 2063-73. doi: 10.2106/JBJS.K.01604. Improved healing of large segmental defects in the rat femur by reverse dynamization in the presence of bone morphogenetic protein-2. Glatt V, Miller M, Ivkovic A, Liu F, Parry N, Griffin D, Vrahas M, Evans C).

In this context, the term "reverse dynamization" will be used to describe stepping up from low to high stiffness of the external fixator construct. This in no way suggests that dynamization of the construct is of no benefit, but this is to be deployed towards the end of the treatment, not at the start. Changing the stiffness of the construct according to the present invention is a simple, ambulatory intervention comprising the steps of loosening the adjacent bolts, followed by inserting, or removing the shims and then retightening the bolts.

The two bars of the external fixator frame disclosed herein are preferably identical parts. They may be produced by injection molding of a high performance, fiber reinforced polymer. When opposed to each other in clamshell fashion and clamped by a set of fastening elements, e.g. bolts and nuts, they form a strong and stiff frame for holding the bone pins. For a human tibia or femur, the length of the frame allows for 45 different positions of the bone pins. Production costs of such a frame are much lower—at least an order of magnitude—than of the conventional external fixators and thus should be affordable in undeveloped countries, where currently only conservative treatments by splinting or casting are viable options of fracture treatment.

In much of the developed world the unpredictable outcomes of conventional external fixation in comparison to plating or nailing have reduced its use to only temporary stabilization of the open fractures, followed by internal fixation. However, if the external fixation by reverse dynamization finds it way from research into clinical practice, reliable and fast healing by external fixation could significantly reduce the cost and the morbidity of multiple interventions currently practiced.

LIST OF FIGURES

FIG. 1: A perspective view of the external fixator according to the present invention showing the frame and six bone pins FIG. 2: A frontal and top views of the external fixator attached to a fractured bone FIG. 3: A perspective view of the bar of the frame showing the inside-facing details of the bone pins clamping features FIG. 4: A perspective view of a section of the bar of the frame with three bone pins crossing at one of the clamping positions FIG. 5: Orthogonal views of a section of the bar of the frame with three bone pins crossing at one of the clamping positions FIG. 6 Cross sectional views of the frame showing the bone pins clamping features of the frame clamped onto the bone pins with the bolts and nuts of the frame FIG. 7: A perspective and view of the clamping shim for obliquely placed bone pins alone and inserted into the frame FIG. 8: Two drill sleeves passed through the frame of the external fixator FIG. 9 A spacer pin protecting the obliquely inserted bone pin from being unintentionally clamped when without the shims FIG. 10: A transverse or T-bar attached to the axial bar for holding bone pins inserted into short bone segments near adjacent joints FIG. 11: An external fixator construct comprising a link connecting two separate bone pins-clamping units

DETAILED DESCRIPTION

FIG. 1 shows the perspective view of the external fixator frame with six bone pins 2 according to the present invention. The frame 1 is comprised of two identical bars 1a and 1b opposed to each other in clamshell fashion and clamped together with a multitude of fastening elements, e.g. bolts and nuts 3, nuts being on the lower side of the frame and thus not visible on this view. At each position for bone pins there are preferably recesses that can accommodate three pins—one can be placed perpendicularly to the long axis of the frame and the other two obliquely. Large recesses 4 at each end of the frame can receive and clamp auxiliary elements of the fixator, e.g. a transverse T-bar.

Figure 2:
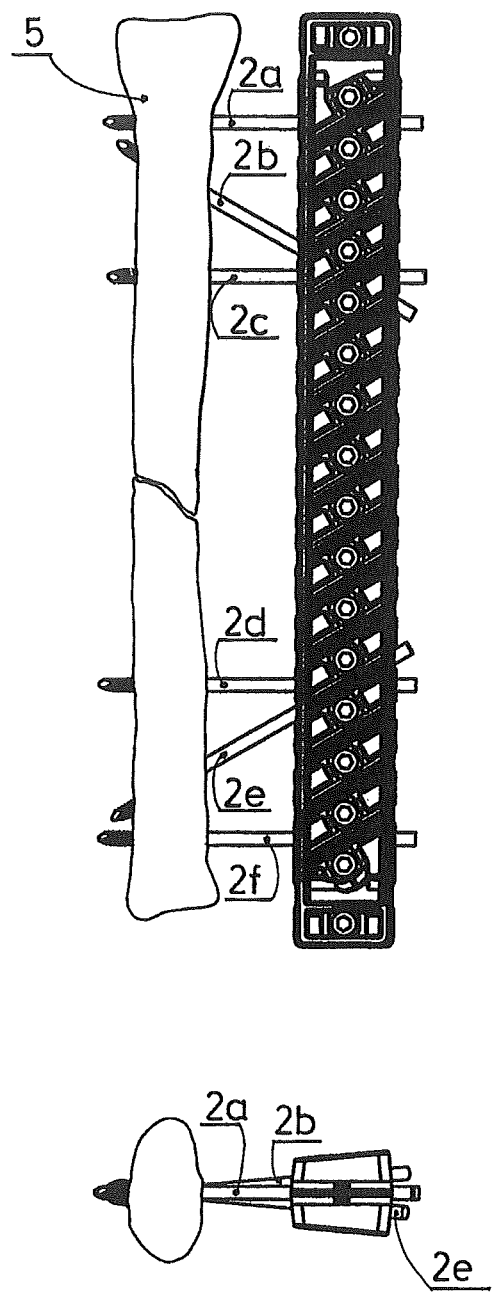

FIG. 2 shows a frontal and a top view of the external fixator attached to a fractured bone 5. While many options exist for placing pins into the bone fragments with a total of 45 choices for the pins, the configuration shown with three pins per bone segment, two of which are perpendicular to the frame, is simple and easy to execute and modulate for overall stiffness. The perpendicular bone pins 2a, 2c, 2d and 2f are in the mid-plane of the external fixator—the oblique bone pins 2b and 2e are angled in the transverse plane, as shown in the top view.

Figure 3:
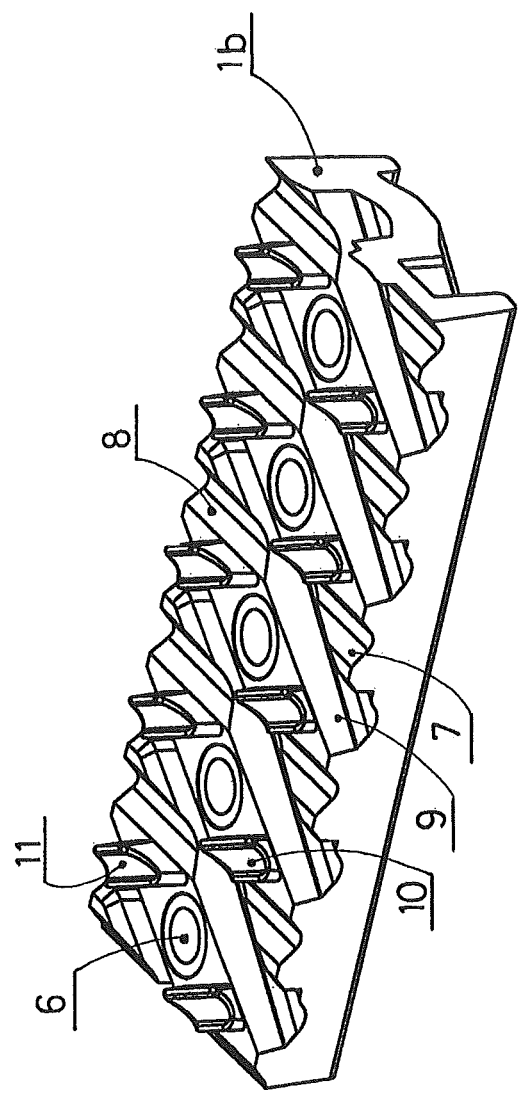

FIG. 3 shows a segment of a frame bar 1b with the inside facing features that allow clamping of the bone pins at any one of the positions and in any of the three orientations. Between any two pin positions there are holes 6 for passing the clamping bolts. For clamping perpendicular bone pins there are V-shaped grooves 7 and 8 at each edge of the bar 1b. Exactly the same recesses exist in the bar 1a (not shown here). A deep V-shaped groove 9 is placed obliquely to the long axis of the frame and its depth also varies across the width of the bar, being shallower on the side that will face bone. This will result in the bone pin entering the bone at about the same line (close to the middle) as the perpendicular bone pins, provided that the distance to the bone is properly chosen. Elevated features 10 and 11, also with a V-shaped groove on the top, will clamp the bone pins seated in the corresponding deep groove of the frame bar 1a (not shown). The depth of the groove 9 is sufficient to allow interference-free crossing of the pins in the groove 9 and in the perpendicular grooves 7 and 8.

Figure 4:
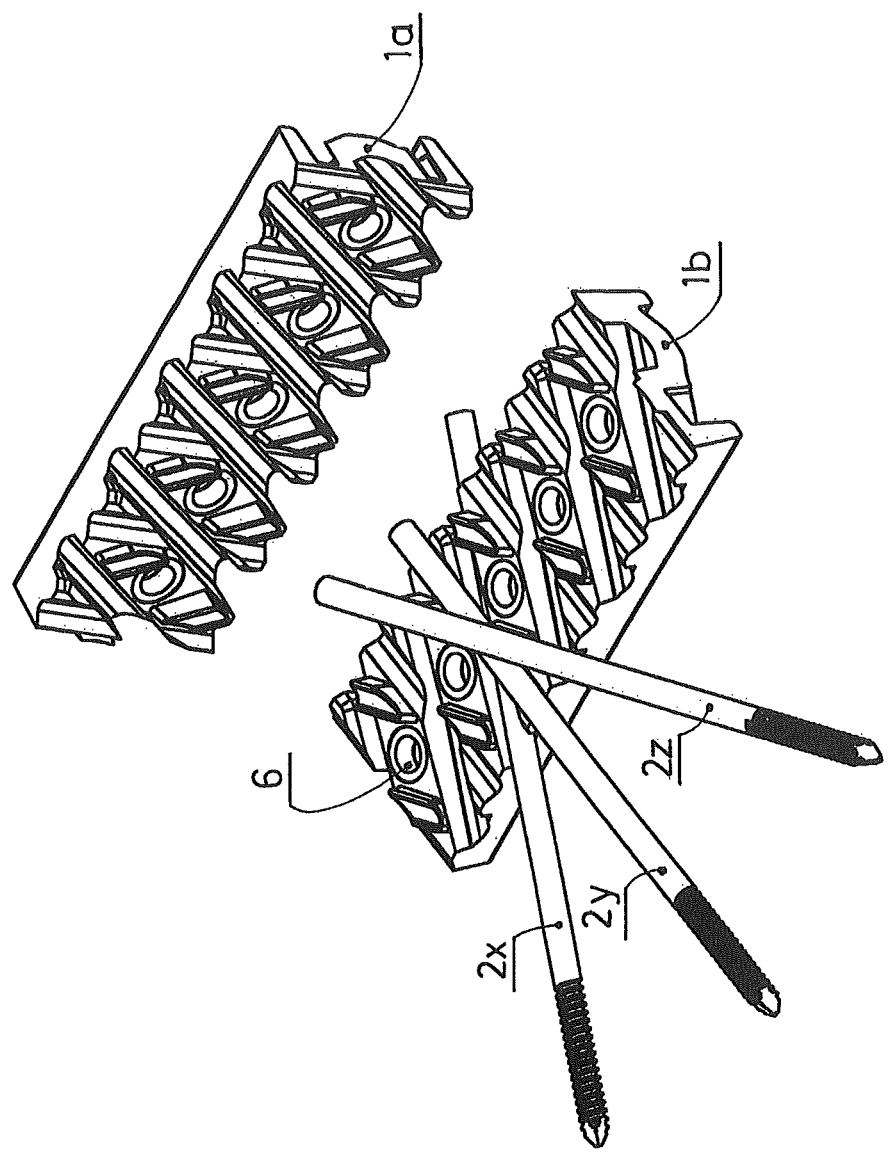

FIG. 4 shows a perspective view of three bone pins 2x, 2y and 2z crossing at a point in mid section of the frame bar 1b, with the corresponding section of the frame bar 1a lifted off and turned by 90 degrees to show the pins.

Between the bone pin positions there are transverse holes 6 for passage of the bolts 3.

Figure 5:
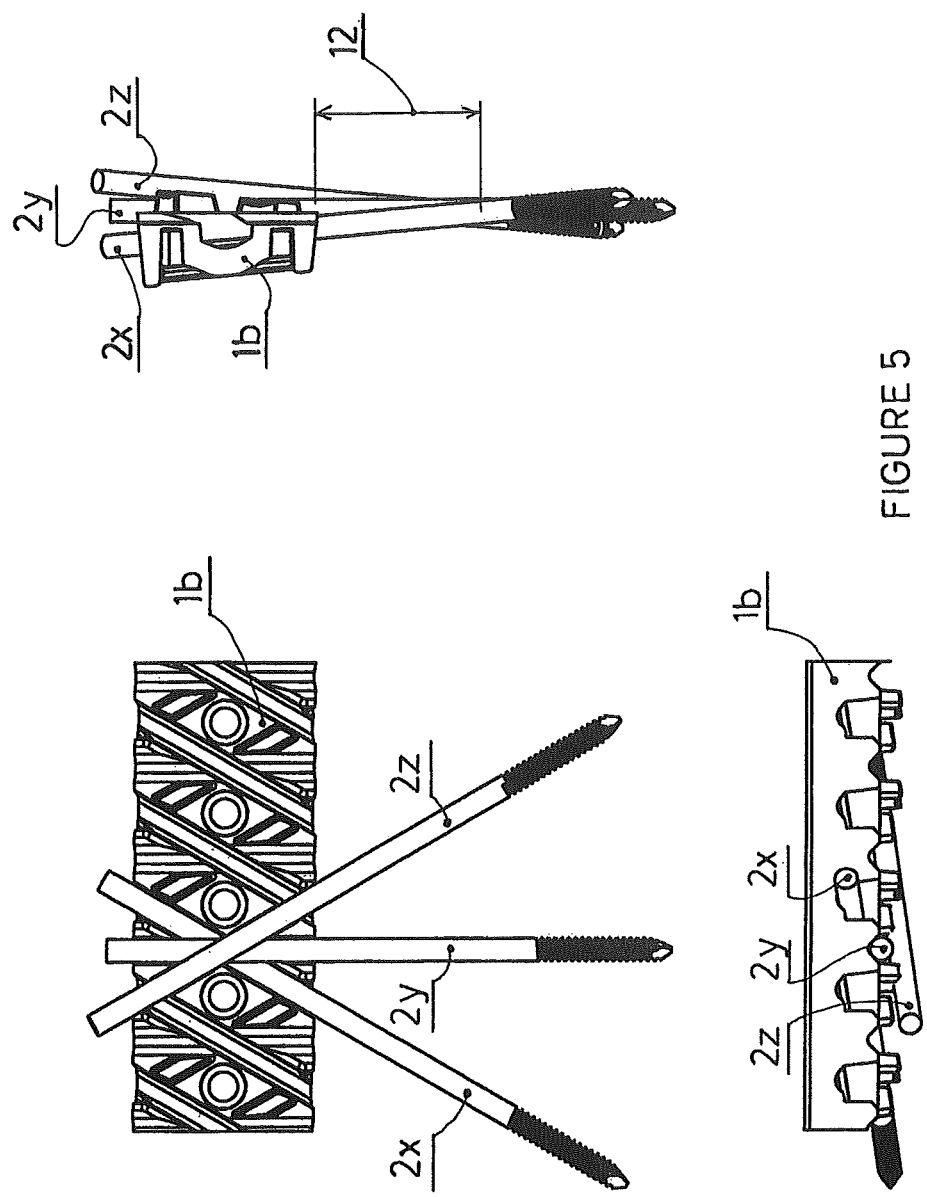

FIG. 5 shows orthogonal views of the frame bar 1b and the three bone pins 2x, 2y and 2z. The distance 12 where the axis of the pins cross in the side view is the ideal distance between the frame and the bone, so that all pins enter the bone at about the same transverse position—about the middle of the bone.

Figure 6:
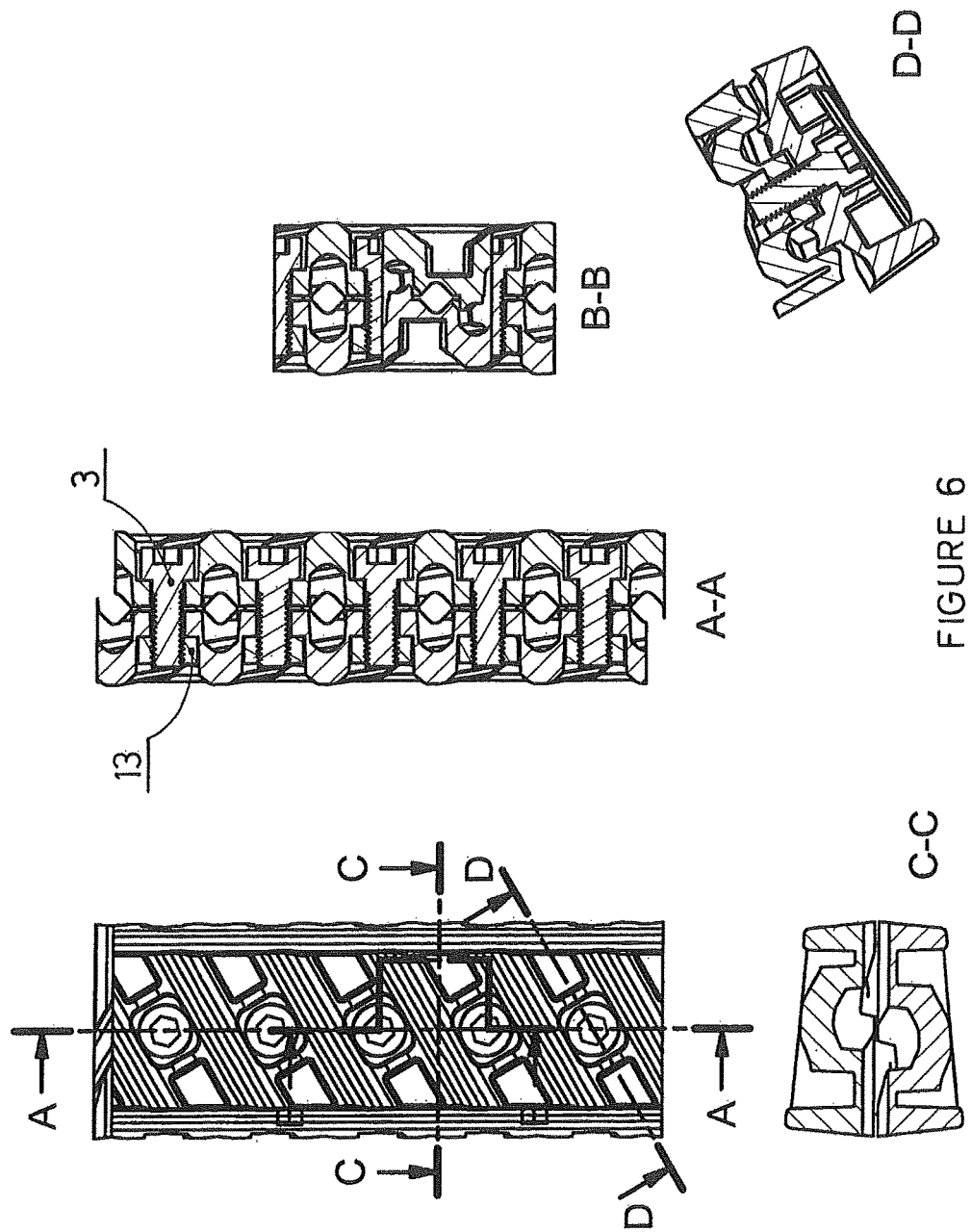

FIG. 6 shows a section of the fixator frame with four different cross sections A-A, B-B, C-C and D-D. The bolts 3 and the nuts 13 are used to clamp the frame and the interposed bone pins together. Nuts are preferably fixed in the frame, by e.g. ultrasonic welding.

Figure 7:
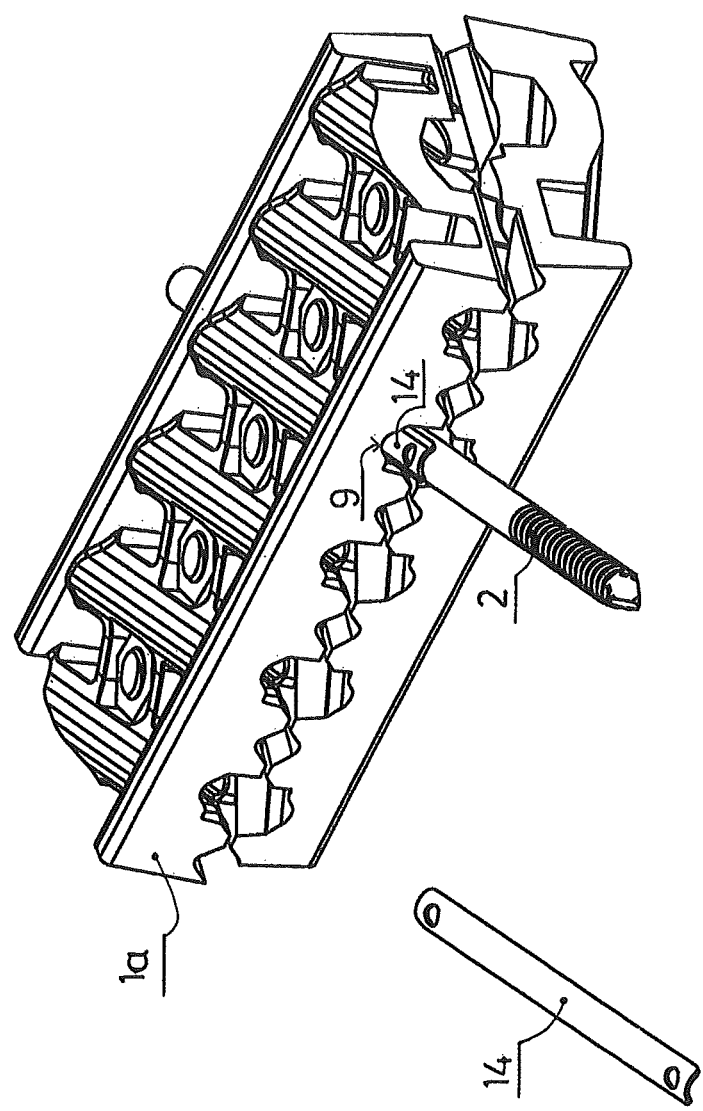

FIG. 7 shows a fixing element, e.g. a shim 14 in the perspective view and also inserted between the bone pin 2 and the groove 9 in the frame bar 1a. The holes 15 in the shim are to facilitate its insertion and removal into/from the intended position along the bone pin.

Figure 8:
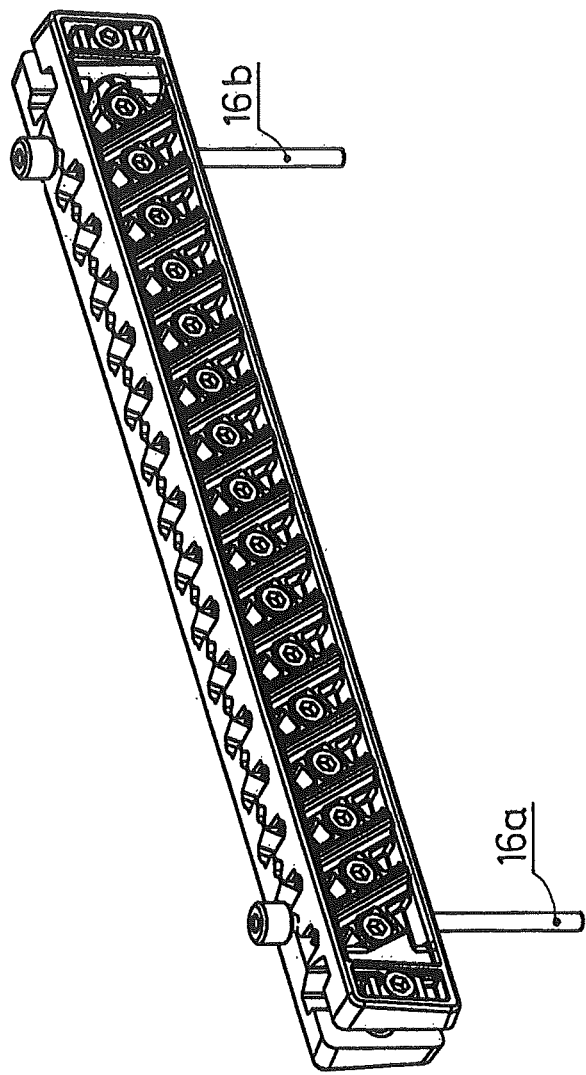

FIG. 8 shows a perspective view of the external fixator according to the present invention with two drill sleeves 16a and 16b clamped in the frame 1 to facilitate pre-drilling of the holes in the bone segments for insertion of the bone pins in the exact positions. The outside diameter of the drill sleeves 16 is the same as that of the pins; the inside corresponds to the diameter of the drill used to pre-drill the bone. The sleeves can be clamped so that their length pointing out from the frame towards the bone is equal to distance 12 of FIG. 5. Before pre-drilling the holes in the bone segments the fracture should be reduced if a single frame as shown here is used to stabilize the fracture.

Figure 9:
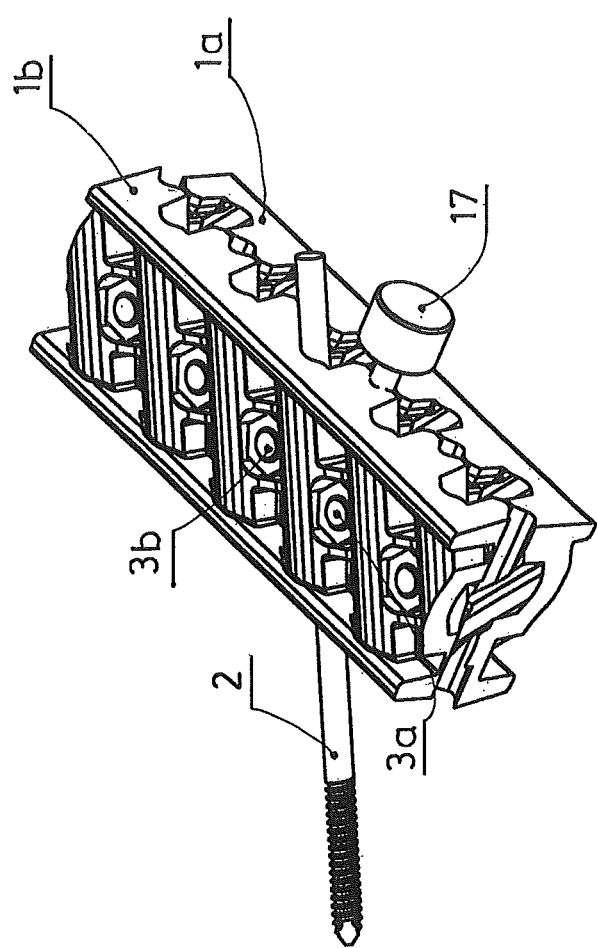

FIG. 9 shows a perspective view of a segment of the frame 1 with a bone pin 2 inserted in an oblique direction. In this position, the pin is not clamped without a shim. However, deformation of the frame bars 1a and 1b, squeezed by the bolts 3a and 3b, could still cause a partial engagement of the bone pin in the frame. To prevent this, a dummy, short pin 17 can be inserted at the same position as the bone pin 1, in the perpendicular direction. This is not needed if there is another bone pin in that location.

Figure 10:
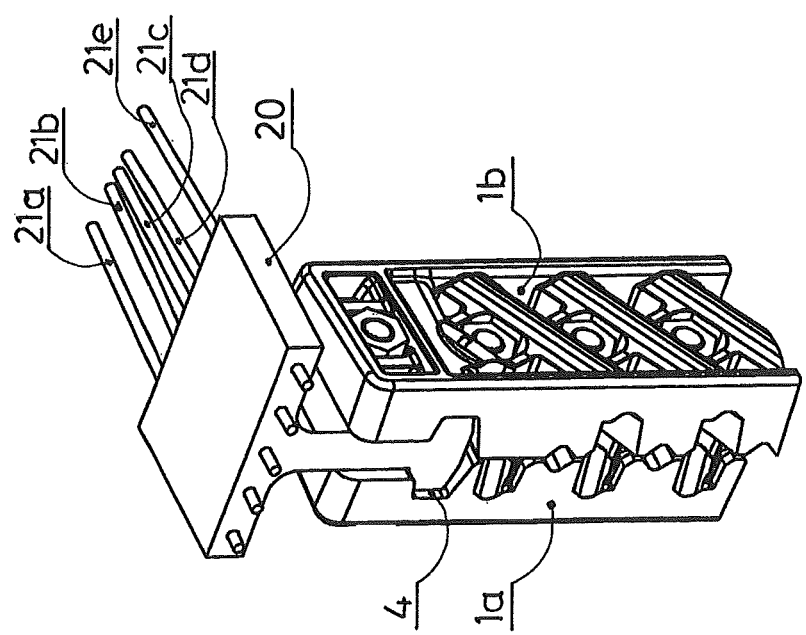

FIG. 10 shows a perspective view of the fixator frame with a T-bar 20 locked in the large recess 4 between the bars 1a and 1b of the main fixator frame. The purpose of this T-bar is to allow placement of bone pins 21a-e into the very end of the fractured, or osteotomized bone.

Figure 11:
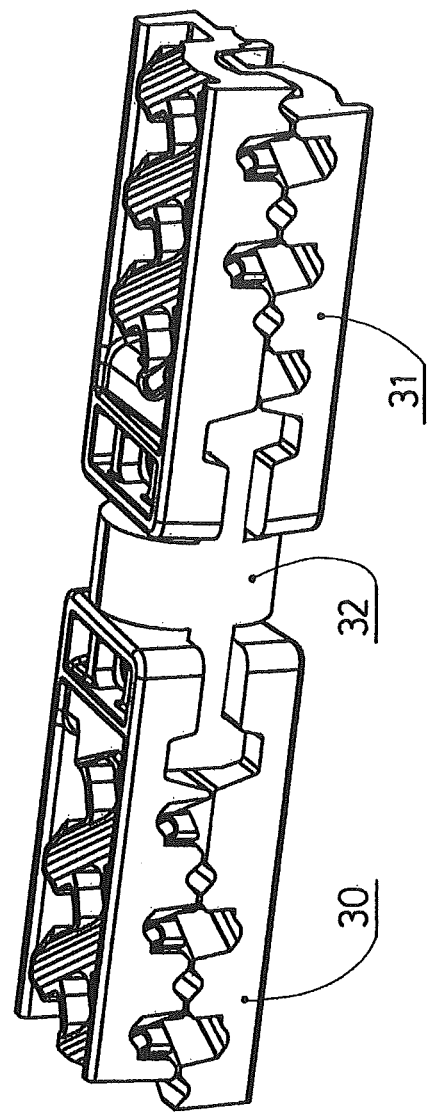

FIG. 11 shows an external fixator frame consisting of two sections 30 and 31, connected by a universal joint 32, shown only schematically. The sections 30 and 31 are just the shorter versions of the frame 1, otherwise of the same construction and with the same functional features. Use of connecting universal joint is common in the art to facilitate more precise reduction of the fracture, should the first one, obtained in the primary surgical intervention, not be adequate. Unfortunately, the production of such a frame entails much higher production costs, so for the undeveloped countries in may not be economically feasible.

The invention discloses an external fixator frame composed of two identical parts, opposed to each other in a clamshell fashion, clamped over interposed bone pins by a set of nuts and bolts providing a stable fixation of the bone pins against bending and axial loads. The bone pins can be inserted through the frame at a multitude of positions, either perpendicularly, or at an angle to the long axis of the frame. Clamping of the fixator frame locks only the bone pins placed perpendicularly to the frame—those inserted at an angle are locked only upon insertion of shims between the pins and the frame. The frame components are injection molded using a high performance, fiber-reinforced polymer. In the proposed method of use, preferably three pins are inserted in each of the bone segments, no more than two parallel to each other. In the initial period of fracture healing, only two pins are locked making the construct stiffness relatively low. After a period of one to two weeks, the third pin is locked by insertion of the shim, increasing the construct stiffness by more than a factor of two in what is referred to as reverse dynamization. In the final phase of the fracture healing, after additional two to three weeks, pins can be either selectively removed, or unlocked in the frame by shim removal to effect conventional dynamization.

The invention claimed is:

1. An external fixator for fixing bone segments into a construct comprising:
a frame (1) consisting of a first bar and a second bar (1a, 1b), wherein the first bar and the second bar are opposed to each other in a clamshell fashion and clamped together by a plurality of fasteners; and
a plurality of bone pins (2) interposed between the first bar and the second bar, wherein the clamping of the first bar and the second bar results in clamping of a subset of the plurality of bone pins interposed between the bars, wherein the plurality of bone pins are at a multitude of pre-set positions, and wherein at least one unclamped bone pin of the plurality of bone pins is effectively clamped by insertion of one or more fixing elements on a surface of the at least one unclamped bone pin of the plurality of bone pins disposed between the first bar and the second bar.

2. The external fixator of claim 1, wherein the plurality of bone pins (2) can be inserted through the frame (1) between the first bar and the second bar at pre-defined positions, wherein the pre-defined positions comprise at least two different angulations with respect to the frame (1).

3. The external fixator of claim 2, wherein the pre-defined positions include (i) a first plurality of grooves perpendicular to a longitudinal axis of the frame and (ii) a second plurality of grooves at an oblique angle to the longitudinal axis of the frame, and wherein each of the second plurality of grooves has a depth which varies along a width of the frame.

4. The external fixator of claim 2, wherein the pre-defined positions include a first position at a first oblique angle to the longitudinal axis of the frame and a second position at a second oblique angle to the longitudinal axis of the frame, wherein the first position is substantially perpendicular to the second position.

5. The external fixator of claim 1, wherein the clamped subset of the plurality of bone pins are disposed between the first bar and the second bar at an angle perpendicular to the longitudinal axis of the frame, and
wherein the at least one unclamped bone pin of the plurality of bone pins disposed between the first bar and the second bar at an oblique angle to the longitudinal axis of the frame remains unclamped.

6. The external fixator of claim 1, wherein each of the plurality of bone pins (2) interposed between the first bar and the second bar is located in at least one of: (i) a mid-plane of the frame, (ii) a first plane transverse to the mid-plane of the frame, and/or (iii) a second plane transverse to the mid-plane of the frame.

7. The external fixator of claim 1, wherein the first bar and the second bar (1a, 1b) are injection molded bars comprising a glass fiber or a carbon fiber reinforced polymer.

8. The external fixator of claim 7, wherein the first bar and the second bar (1a, 1b) are identical.

9. The external fixator of claim 1, wherein the plurality of fasteners comprises bolts and nuts (3).

10. The external fixator of claim 1, wherein the one or more fixing elements are shims (14).

11. An external fixator for fixing bone segments into a construct comprising:
- a frame (1) consisting of a first bar and a second bar (1a, 1b), wherein the first bar and the second bar are opposed to each other in a clamshell fashion and clamped together by a plurality of fasteners; and
- a plurality of bone pins (2) interposed between the first bar and the second bar, wherein the clamping of the first bar and the second bar results in clamping of a subset of the plurality of bone pins interposed between the bars, wherein the plurality of bone pins are at a multitude of pre-set positions, wherein the plurality of bone pins (2) can be inserted through the frame (1) between the first bar and the second bar at pre-defined positions, wherein the pre-defined positions comprise at least two different angulations with respect to the frame (1), wherein the pre-defined positions include (i) a first plurality of grooves perpendicular to a longitudinal axis of the frame and (ii) a second plurality of grooves at an oblique angle to the longitudinal axis of the frame, and wherein each of the second plurality of grooves has a depth which varies along a width of the frame.

* * * * *